(12) United States Patent
Munson

(10) Patent No.: US 8,528,833 B2
(45) Date of Patent: Sep. 10, 2013

(54) PORTABLE HEATING PAD

(75) Inventor: Ryan Robert Munson, Tampa, FL (US)

(73) Assignee: Ryan R. Munson, Tampa, FL (US)

( * ) Notice: Subject to any disclaimer, the term of this patent is extended or adjusted under 35 U.S.C. 154(b) by 321 days.

(21) Appl. No.: 12/562,097

(22) Filed: Sep. 17, 2009

(65) Prior Publication Data
US 2011/0061839 A1  Mar. 17, 2011

(51) Int. Cl.
*F28D 15/00* (2006.01)
*F28D 21/00* (2006.01)
*A41D 13/005* (2006.01)

(52) U.S. Cl.
USPC ............ 237/2 R; 237/71; 237/77; 126/204; 126/208; 126/210; 36/2.6; 165/46; 122/26

(58) Field of Classification Search
USPC .............. 126/204, 208, 210; 36/2.6; 122/26; 165/46; 237/2 R, 71, 77
IPC ...................... F28D 15/00, 21/00; A41D 13/005
See application file for complete search history.

(56) References Cited

U.S. PATENT DOCUMENTS

| | | | | |
|---|---|---|---|---|
| 156,117 A * | 10/1874 | Angresius | ......................... | 36/2.6 |
| 1,202,605 A * | 10/1916 | Storm, Jr. | ...................... | 126/204 |
| 2,590,212 A | 3/1952 | Samuels | | |
| 2,652,824 A * | 9/1953 | Hopp | ........................... | 126/208 |
| 2,764,969 A * | 10/1956 | Weiss | ........................... | 126/208 |
| 2,800,891 A * | 7/1957 | Rehorn | ........................ | 126/208 |
| 2,996,062 A * | 8/1961 | Weiss | ........................... | 126/208 |
| 3,110,301 A * | 11/1963 | Bricker | ........................ | 126/208 |
| 3,159,158 A * | 12/1964 | Baker | ........................... | 126/208 |
| 3,406,678 A * | 10/1968 | Hanks | ........................... | 126/208 |
| 3,438,069 A * | 4/1969 | Long | ................................. | 5/422 |
| 3,457,908 A * | 7/1969 | Hamatani et al. | ............. | 126/208 |
| 3,894,213 A | 7/1975 | Agarwala | | |
| 4,077,390 A | 3/1978 | Stanley et al. | | |
| 4,817,707 A * | 4/1989 | Aoyama et al. | ................. | 165/46 |
| 4,821,354 A * | 4/1989 | Little | ................................ | 5/422 |
| 5,320,164 A * | 6/1994 | Szczesuil et al. | .............. | 165/46 |
| 5,562,604 A | 10/1996 | Yablon et al. | | |
| 5,755,275 A * | 5/1998 | Rose et al. | ....................... | 165/46 |
| 5,878,807 A * | 3/1999 | Takahashi | ....................... | 165/46 |
| 5,901,698 A * | 5/1999 | Welles | ......................... | 126/208 |
| 6,062,210 A * | 5/2000 | Welles | ......................... | 126/208 |
| 6,550,471 B2 * | 4/2003 | Szymocha et al. | ............ | 126/208 |

(Continued)

FOREIGN PATENT DOCUMENTS

EP       76077 A2 *  4/1983
EP       76078 A2 *  4/1983

(Continued)

*Primary Examiner* — Steven B McAllister
*Assistant Examiner* — Daniel E Namay

(57) ABSTRACT

A portable heating system used to heat a person while in cold environments. A heating unit containing a fuel combustion chamber and a heat exchanger oxidizes a fuel to produce heat. The heat from the oxidation process is transferred to the fluid using the heat exchanger. The fluid either boils or simply becomes less dense than cooler fluid in the heat exchanger and thus more buoyant. Convection moves the heated fluid upwards in to a thin bladder encapsulating the fluid and held against a person. The elevated kinetic energy in the bladder creates an entropy differential to the person. This differential allows the kinetic energy in the bladder to flow to the person thus warming them. The fluid now having less energy, now denser, flows back down the bladder to the heating unit by gravity.

5 Claims, 3 Drawing Sheets

(56) References Cited

U.S. PATENT DOCUMENTS

| | | | |
|---|---|---|---|
| 6,752,203 B2 * | 6/2004 | Kurita | 165/169 |
| 6,772,825 B2 * | 8/2004 | Lachenbruch et al. | 165/46 |
| 6,957,697 B2 * | 10/2005 | Chambers | 165/297 |
| 6,987,928 B2 * | 1/2006 | Shields | 392/379 |
| 7,373,969 B2 * | 5/2008 | Chambers | 165/297 |
| 7,775,204 B2 * | 8/2010 | Chen | 126/204 |
| 7,823,625 B2 * | 11/2010 | Gammons | 165/46 |
| 2001/0011585 A1 * | 8/2001 | Cassidy et al. | 165/46 |
| 2001/0018915 A1 * | 9/2001 | Nuckols et al. | 126/204 |
| 2002/0096311 A1 * | 7/2002 | Kushnir et al. | 165/46 |
| 2003/0131967 A1 * | 7/2003 | Weder | 165/46 |
| 2003/0192669 A1 * | 10/2003 | Wu | 165/46 |
| 2008/0063771 A1 * | 3/2008 | Dumm | 426/522 |
| 2009/0133853 A1 * | 5/2009 | Gammons | 165/104.11 |
| 2009/0159238 A1 * | 6/2009 | Ko et al. | 165/46 |
| 2009/0199571 A1 * | 8/2009 | Creech et al. | 62/3.2 |
| 2010/0031428 A1 * | 2/2010 | Paull | 2/458 |
| 2010/0096102 A1 * | 4/2010 | Chiu et al. | 165/46 |

FOREIGN PATENT DOCUMENTS

| | | | |
|---|---|---|---|
| EP | 76079 A2 * | 4/1983 | |
| JP | 55116096 A * | 9/1980 | |
| JP | 56068794 A * | 6/1981 | |
| JP | 11050315 A * | 2/1999 | |
| JP | 11158709 A * | 6/1999 | |
| JP | 2000014692 A * | 1/2000 | |
| JP | 2001049507 A * | 2/2001 | |
| JP | 2001115314 A * | 4/2001 | |
| WO | WO 9428834 A1 * | 12/1994 | |
| WO | WO 2005055751 A1 * | 6/2005 | |

* cited by examiner

PORTABLE HEATING PAD

BACKGROUND OF THE INVENTION

1. Field of the Invention

The invention relates to human body temperature management systems and in particular to devices for therapeutically heating.

2. Description of the Prior Art

The human body is constantly producing heat when metabolizing food. This heat is an import part of bodily function and sometimes the human body can not produce enough heat and fall subject to hypothermia. Core body temperature is maintained near a constant level through biologic homeostasis. But when the body is exposed to cold its internal mechanisms may be unable to replenish the heat that is being lost to the environment.

U.S. Pat. No. 2,590,212 to Samuels (1952) is a flexible therapeutic heating pad device for heating a body part. It uses electric resistance heating coils to produce heat. The coils are embedded in a flexible pad that is worn or pressed against the body part to be heated. This device requires a large amount of electrical power to operate limiting its portability while in use.

U.S. Pat. No. 3,894,213 to Agarwala (1975) is a heating pad using a fluid, an electrically heated reservoir, a circulating pump and a fluid filled pad with an inlet and an outlet for the fluid to flow. The fluid is heated in the reservoir then pumped in to the inlet of the pad. There it circulates through the pad warming the person and then exits the pad via the outlet and returns to the reservoir. This device requires electrical power to heat the fluid and to pump the fluid through the pad.

U.S. Pat. No. 5,562,604 to Yablon (1996) is a portable therapeutic device for treating a patient undergoing hot or cold therapy. This device is comprised of a flexible containment bag means comprising a sealed closed-loop fluid channel containing a liquid, an electromagnetic pumping means, a self-contained source of a therapeutic temperature and microprocessor temperature control. While this device is configured for heating the liquid is heated in the temperature control unit. The heated liquid is pumped to the flexible containment bag using an electromagnetic pump. The flexible containment bag is warn against the person receiving the therapy. Heat is transferred from the bag which contains the liquid to the person. The liquid cools off and is returned to the self-contained source of therapeutic temperature control. This portable therapeutic device relies on an electromagnetic pump to move the liquid. Electromagnetic pumps require that the liquid it pumps be a good electrical conductor and uses electrical power to produce the magnet field to pump the liquid.

U.S. Pat. No. 4,077,390 to Stanley et al (1978) a heating pad is made by enclosing a supersaturated aqueous sodium acetate solution with an activator strip in a flexible container. The heating pad is charged by applying heat to the pad until the sodium acetate is completely dissolved in the water. As the pad is cooled the sodium acetate remains dissolved in the water forming the supercooled solution. When the user wants to release the latent heat trapped in the solution he activates the flexible metal strip which causes the solution to crystallize. Heat is released until the crystallization process finishes.

All of the aforementioned devices have the ability to heat a person. Each one has it's own method of accomplishing basically the same thing. Likewise each method has strengths and limitations. The Samuels device uses electrical resistance heating coils to produce heat. This method uses large amounts of electrical power making it infeasible for portable heating. The Agarwala device electrically heats a liquid and uses an electrically powered pump to move the heated liquid through a bladder. This method requires a large amount of electrical power and added weight of a pump both of which limit the portability of the device. The Stanley et al device is very portable for a one time use. However the amount of heat it produces is very limited and recharging the device takes a lot of time and requires a much larger device like a stove. None of these inventions use a form of combustion to produce heat. Typically combustion produces an intensely high temperature heat that will burn the skin of a person if they come in contact with it. This is unfortunate because a small amount of fuel like propane can produce a large amount of heat for a long period of time. However this intensely high temperature heat can be spread over a larger area to produce a safe and comfortable amount of heat for a person.

SUMMARY OF THE INVENTION

The present invention provides a portable heating system to add heat to a person when their body can not produce enough heat through biologic homeostasis. The invention provides a pliant bladder to be pressed against the person to be heated, a fluid used as a transfer medium and a combustion based heating unit. The bladder is a thin fluid filled container with vertical channels to guide the flow of the fluid up and down. In the heating unit a fuel such as propane is combusted either by open flame or catalytic process to produce an intense heat. This combustion is done inside of a heat exchanger where heat from the combustion is transferred in to the fluid. The addition of the heat to the fluid causes it to expand and become less dense and thus more buoyant than the cooler fluid. Potentially the fluid could be in liquid form while in the heating unit and a gas when it exists. Convection moves heated fluid upwards in the bladder to the person being heated as it is simultaneously replaced by cooler fluid returning either by gravity or a wicking system. The now heated fluid is warmer then the body temperature of the person being heated allowing transfer of heat energy from the fluid in the bladder to move to the person. This cools the fluid and makes it more dense. Fluid in gaseous form may condense back in to a liquid when its heat is transferred. Heavier fluid will flow down to the heating unit.

This portable heating pad is a novel device for warming people in cold environmental conditions. It has the ability to produce a proper amount of heat spread comfortably over an area of the human body for long periods of time while remaining very light weight. This is ideal for a person that needs to perform a task outside in the winter months. Often when electricians or plumbers work outside in the cold their hands lose dexterity and become unable to complete their task. Adding heat to their back raises their core body temperature and improves circulation to the hands returning dexterity.

DESCRIPTION OF THE PREFERRED EMBODIMENT

Figure 1:
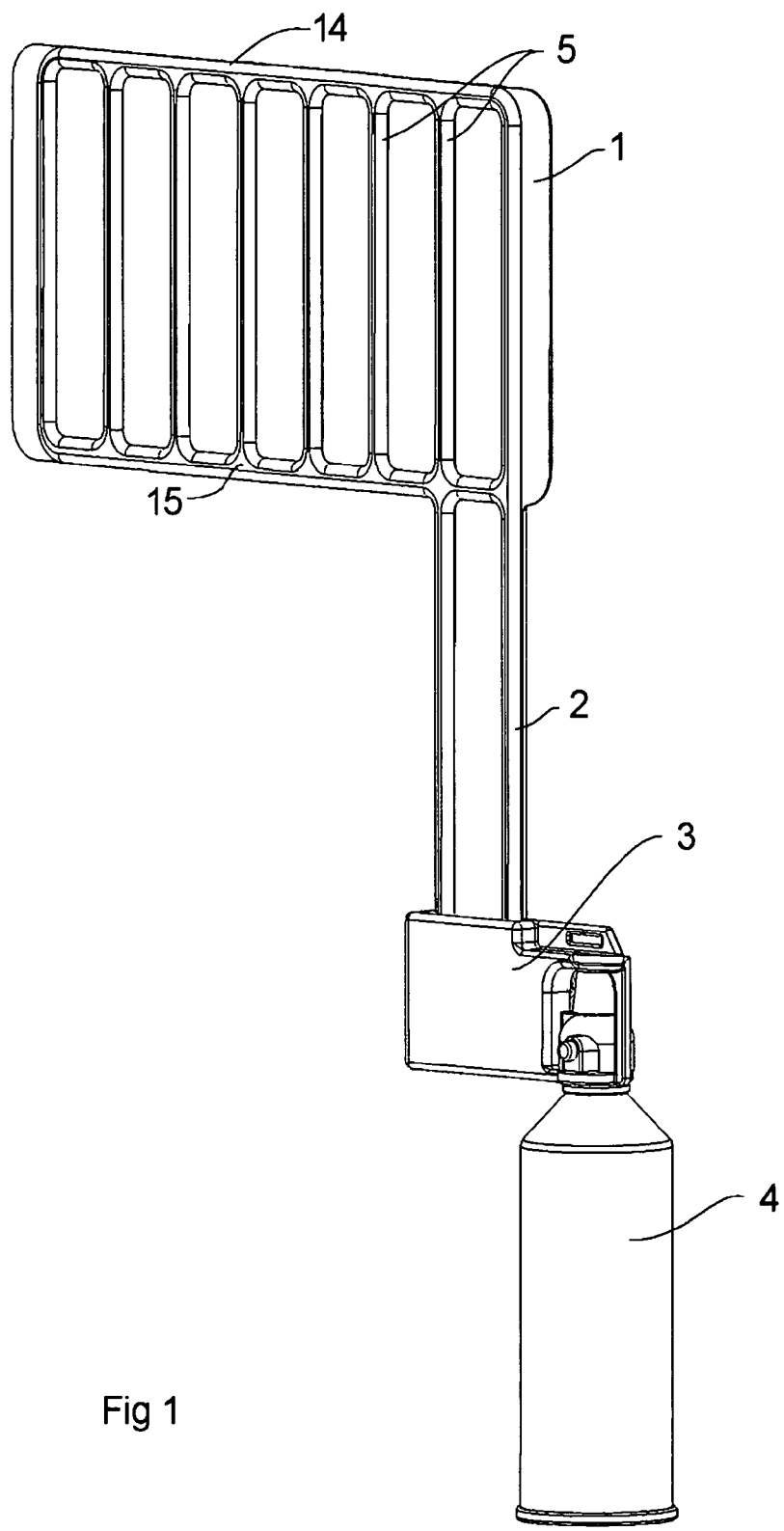
FIG. 1 is a perspective view of the preferred embodiment.

FIG. 1 depicts a perspective view of one preferred embodiment of the present invention. The bladder (1) is comprised of two sheets of polyurethane which are sandwiched and sealed at the edges using RF welding. Further seals within the bladder (1) are added in a vertical manner to create channels (5). The channels (5) may be disposed between a proximate manifold (15) located near the heating unit(3), and a distal manifold (14) located on a side of the bladder (1) opposite the proximate manifold (15). This gives the bladder (1) structure and are used to guide the liquid in the bladder up and down. In this preferred embodiment the liquid in the bladder (1) is water which was chosen for its low viscosity and thermal characteristics. The heating unit (3) is a heat exchanger with a combustion chamber and a fluid channel with an inlet and an outlet containing water. Fuel for combustion is stored in the can (4). The present invention must be oriented so that it pitches down with the heating unit (3) on the bottom. This ensures that the warmed water floats towards the bladder (1). In this preferred embodiment the bladder (1) has two tubes (2) connecting it to the heating unit (3). These tubes (2) give passage for the water to move from the heating unit (3) to the bladder (1) in a closed circuit. One tube (2) goes to the inlet of the heating unit (3) and the other the outlet. When the water in the heating unit (3) is heated up by the combustion process it expands becoming lighter and more buoyant. The now lighter water floats up and out of the heating unit (3) outlet, through the tube (2) and up to the bladder (1). At least one full-length channel (5) spans from the proximate manifold (15) to the distal manifold (14) in the bladder (1) to ensure that the water floats all the way up to the top of the bladder (1) with little interaction with other water molecules in the bladder (1). This method of passive heat exchange based on natural convection which circulates liquid in a vertical closed-loop circuit without requiring a conventional pump is called a thermosyphon.

Figure 2:
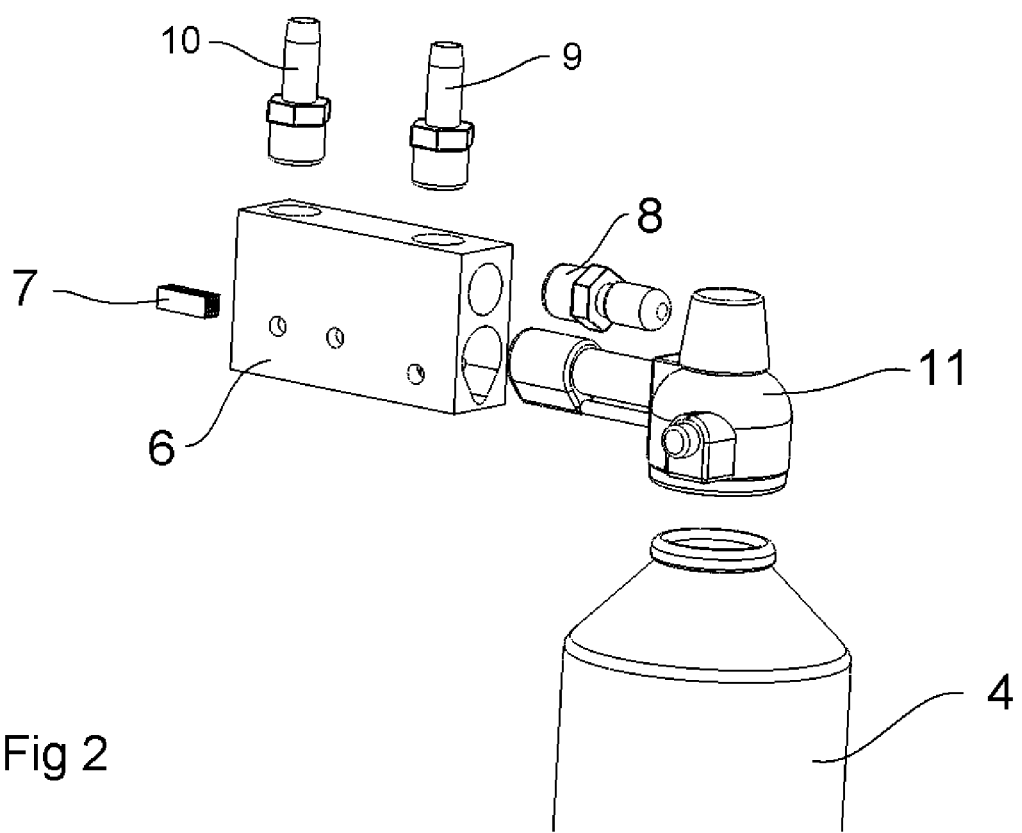
FIG. 2 is an exploded partial perspective view of the heating unit with the enclosure removed.

FIG. 2 is an exploded partial perspective view of the heating unit with the enclosure removed incorporated in the present invention giving a more detailed view of the heating unit then FIG. 1. The heat exchanger (6) is an aluminum manifold and a combustion chamber with an inlet (10) and an outlet (9) hole at the top which holds the water separate from the combustion chamber. A block of catalytic material (7) is contained in the combustion chamber of the heat exchanger (6). A control valve (11) is used to regulate the amount of fuel that is added to the combustion chamber. A can (4) stores the fuel for combustion. In the preferred embodiment the fuel is propane. When in normal operation, fuel from the can (4) travels out of the can (4) through the control valve (11) then to the combustion chamber of the heat exchanger (6). While in the combustion chamber the fuel comes in contact with the catalytic material (7). The catalytic material (7) has the ability to oxidize the propane fuel which produces an intense heat. Heat from the oxidation process heats the surrounding aluminum of the heat exchanger (6). Aluminum is an excellent conductor of heat so the heat is quickly transferred to the water in the heat exchanger (6). The heated water is now more buoyant and floats out of the outlet (9) while colder denser water sinks in through inlet (10). A schrader valve (8) is used to add water to the system while keeping the system sealed.

Figure 3:
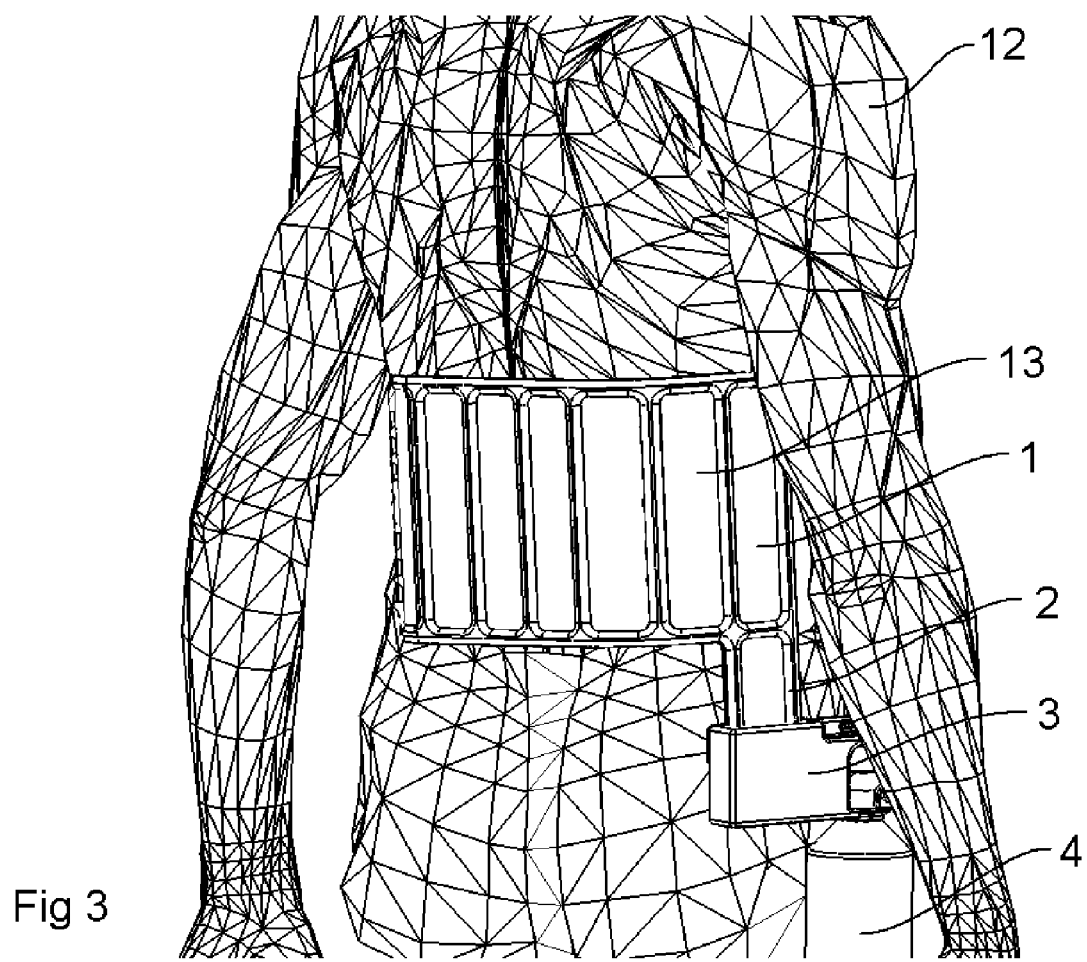
FIG. 3 is a perspective view of the preferred embodiment on a persons back.

FIG. 3 is a perspective view of the preferred embodiment attached to a persons back. The present invention (13) is attached to the back of a person (12) with the pliant bladder (1) covering the lower back of the person (12). When a person (12) wears the present invention (13) in this configuration heat produced by the present invention (13) is absorbed through their back.

What is claimed is:

1. A passive flow portable heating system comprising,
a combustion powered heating unit; and
a heat transfer fluid; and a bladder comprising a plurality of channels in fluid communication with the heating unit,
wherein the heating unit and the plurality of heating channels form at least part of a heating circuit, and
wherein the bladder forms a substantially rectangular waist belt, the bladder comprising a manifold proximate to the heating unit, a manifold distal to the heating unit and parallel to the proximate manifold, the channels fluidly connecting the proximate & distal manifolds, and
wherein when the heating unit is disposed at a lower elevation than the bladder, when the bladder abuts a heat recipient, and when the heating circuit comprises a heat transfer fluid, the heating system forms a thermosyphon effective to heat the recipient.

2. The passive flow portable heating system of claim 1, wherein the bladder comprises a pliant polymeric material and thereby effective to conform to a contour of various heat recipients.

3. The passive flow portable heating system of claim 1, wherein the plurality of channels are parallel.

4. The passive flow portable heating system of claim 1, wherein the bladder further comprises a pliant material configured to form the plurality of channels.

5. The passive flow portable heating system of claim 1, wherein the bladder comprises a planar shape when unflexed.

* * * * *